US008066026B2

(12) United States Patent
Grenaway et al.

(10) Patent No.: US 8,066,026 B2
(45) Date of Patent: Nov. 29, 2011

(54) DIAPHRAGM CONTROLLED BYPASS VALVE

(75) Inventors: John R. Grenaway, Edwardsville, IL (US); Mark K. Hamm, Cullman, AL (US); William Clinton Osteen, Hartselle, AL (US)

(73) Assignee: Tyco Values & Controls LP, Houston, TX (US)

( * ) Notice: Subject to any disclaimer, the term of this patent is extended or adjusted under 35 U.S.C. 154(b) by 697 days.

(21) Appl. No.: 12/117,524

(22) Filed: May 8, 2008

(65) Prior Publication Data

US 2009/0278064 A1 Nov. 12, 2009

(51) Int. Cl.
*G05D 11/00* (2006.01)

(52) U.S. Cl. ........... 137/115.26; 137/87.01; 137/118.06; 251/77

(58) Field of Classification Search ........... 251/77; 137/87.01, 118.06, 115.13, 115.26, 116.3, 137/116.5; 33/77
See application file for complete search history.

(56) References Cited

U.S. PATENT DOCUMENTS

| | | | | |
|---|---|---|---|---|
| 1,737,428 A * | 11/1929 | Mercur | ........................ | 137/116.3 |
| 2,213,789 A * | 9/1940 | Wilkins | ........................ | 137/116.3 |
| 2,707,966 A * | 5/1955 | Taplin | ........................ | 137/116.5 |
| 3,468,341 A * | 9/1969 | Newcomb et al. | ........... | 137/625.3 |
| 3,470,910 A | 10/1969 | Loveless | | |
| 3,495,619 A * | 2/1970 | Iizumi | ........................ | 137/489.5 |
| 3,578,019 A | 5/1971 | Turolla | | |
| 3,756,264 A * | 9/1973 | Fisher | ........................ | 137/116.3 |
| 3,848,630 A | 11/1974 | Weise | | |
| 3,892,389 A | 7/1975 | Contastin | | |
| 4,624,277 A * | 11/1986 | Veite | ........................ | 137/116.3 |
| 5,467,754 A | 11/1995 | Beck et al. | | |
| 5,800,381 A | 9/1998 | Ognier | | |
| 6,554,017 B2 * | 4/2003 | Berger | ........................ | 137/116.5 |
| 2007/0137705 A1 * | 6/2007 | Chen | ........................ | 137/115.13 |

FOREIGN PATENT DOCUMENTS

GB 363114 A1 12/1931

* cited by examiner

*Primary Examiner* — John Fristoe, Jr.
*Assistant Examiner* — Marina Tietjen

(57) ABSTRACT

A diaphragm controlled bypass valve includes a diaphragm valve portion and a needle valve portion. The diaphragm valve portion regulates pressurized gas supplied from a pump to determine whether or not to open or close a needle valve. The needle valve portion includes an inlet port, an outlet port and a flow pathway defined between the inlet and outlet ports. A needle pin is disposed within the flow pathway and is coupled to a diaphragm positioned within the diaphragm valve portion. When the diaphragm is displaced in response to changes in pressure, the needle valve pin is likewise displaced which opens and closes the flow pathway.

18 Claims, 3 Drawing Sheets

DIAPHRAGM CONTROLLED BYPASS VALVE

FIELD OF THE INVENTION

Embodiments of the invention relate to field of valves and the construction thereof. More particularly, embodiments of the invention relate to a diaphragm controlled bypass valve used to regulate the flow of gas from an external source.

DISCUSSION OF RELATED ART

In laparoscopic surgery, a device such as a trocar is used to introduce various surgical instruments into a patient's abdomen. An insufflating gas, for example $CO_2$, is also introduced into the abdominal cavity to raise the cavity wall away from vital organs to avoid any unnecessary contact during the surgical procedure. This gas is usually supplied by a pump or gas source at a pressure of about 25 psi and is supplied to a patient's abdomen using a flexible tube or conduit. A Verres needle inserted into a patient's abdominal cavity supplies the gas from the pump to the abdomen which is maintained at a pressure of about 10-12 mmHG. The pressurized gas supplied to the abdominal cavity is monitored to ensure that pressure within the cavity is maintained within a desired pressure range. Pressure changes in a patient's abdominal cavity during surgery may be as small as ±1 mmHG. Existing systems do not detect these small pressure changes in the abdominal cavity nor do they automatically adjust the flow of gas to the abdomen based on such changes.

Pressure regulators in the form of diaphragm valves utilize an extended membrane to open and close a flow pathway. These valves have moveable diaphragms to control process flow, such as a gas, and are commonly used for processing systems used in pharmaceutical, biotechnical, chemical, food, and semiconductor industries. Although diaphragm valves are reliable and sensitive to slight variations in pressure, they are usually only configured to open and close at certain pressure levels. That is, when a particular pressure level is reached the valve either opens or closes. The objective in the above-referenced surgical procedure is to regulate the flow of pressurized gas to maintain insufflation of a patient's abdomen. In these applications, the valve which controls the flow of pressurized gas to the surgical device typically remains in an open position to regulate the amount of pressurized gas to the system. Accordingly, a valve employed in these systems must be configured to remain in an open position and regulate the amount of pressurized gas to a patient's abdomen. These systems typically monitor the supply line gas pressure coming from the pump or gas source to the surgical device rather than monitoring a patient's abdominal pressure. When the abdominal pressure falls below a desired level, the valve must be configured to react quickly to allow pressurized gas to flow to the surgical device to increase pressure in the patient's abdomen. In addition, when the abdominal pressure increases above a desired level the valve must be configured to react quickly and allow pressurized gas to be diverted away from a patient's abdomen. Thus, there is a need for a valve that maintains a desired pressure range while being sensitive enough to respond rapidly to pressure changes during surgical procedures. There is also a need for a valve to control the flow of pressurized gas from a pump or gas source based on a patient's abdominal pressure rather than supply line pressure.

SUMMARY OF THE INVENTION

Exemplary embodiments of the present invention are directed to a diaphragm controlled bypass valve. In an exemplary embodiment, the diaphragm controlled bypass valve includes a first valve housing having an inlet, an outlet and a flow pathway defined between the inlet and the outlet. A needle valve pin is disposed at least partially within the flow pathway. A valve seat is disposed within the first valve housing and is configured to receive a portion of the needle valve pin to close the flow path. A second valve housing is connected to the first valve housing. A diaphragm extends radially within the second valve housing. A first pressure chamber is defined between the diaphragm and the second valve housing. A second pressure chamber is defined between the diaphragm and the first valve housing. A sensing line is connected to the second pressure chamber and is configured to provide a pressure change to the second pressure chamber to displace the diaphragm within the first pressure chamber. A shaft assembly is disposed between the diaphragm and the needle pin such that displacement of the diaphragm within the second pressure chamber moves the shaft to open and close the needle valve.

DESCRIPTION OF EMBODIMENTS

Figure 1:
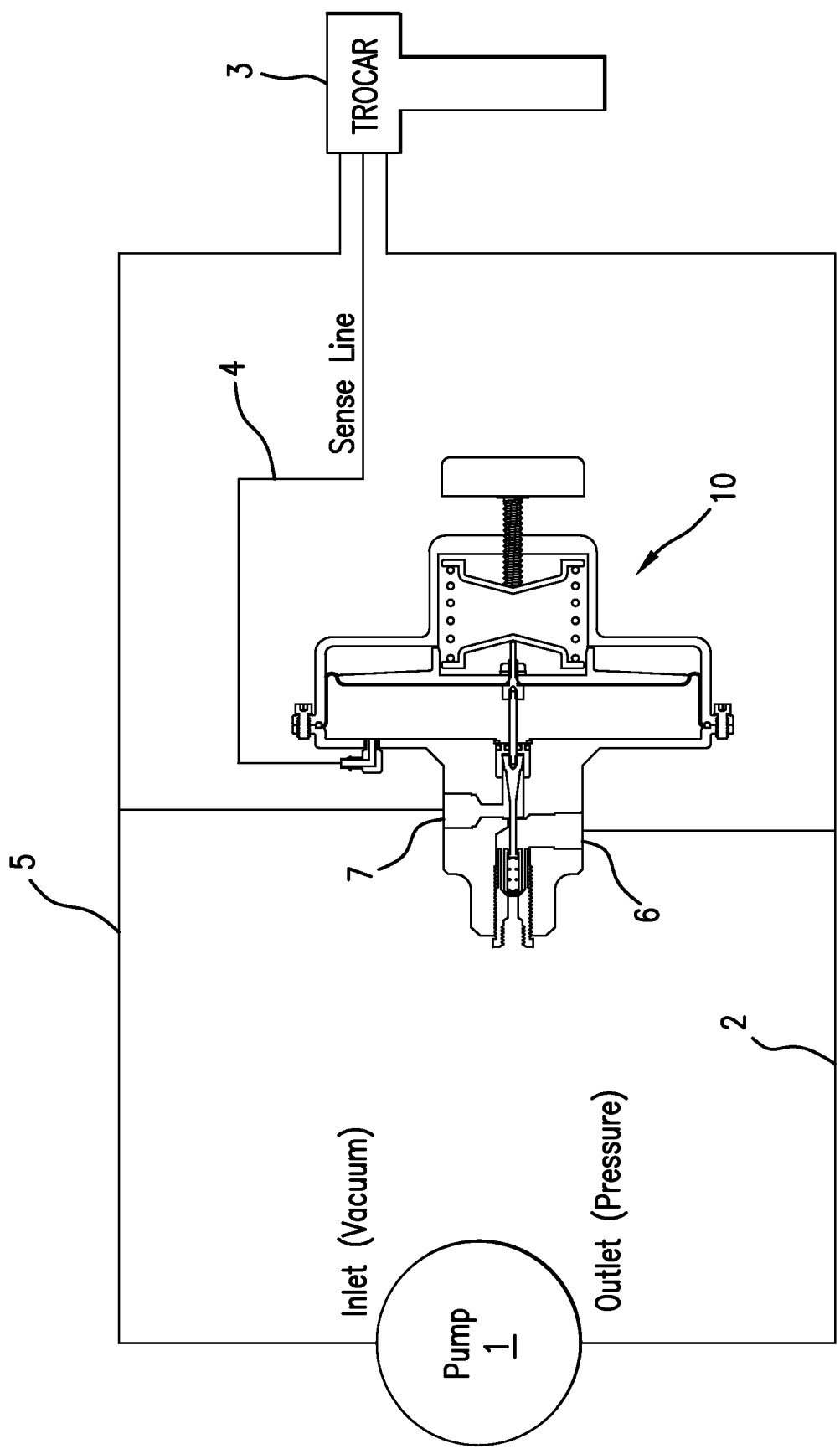
FIG. 1 is a block diagram of a diaphragm controlled bypass valve positioned within an exemplary surgical application in accordance with the present invention.

The present invention will now be described more fully hereinafter with reference to the accompanying drawings, in which preferred embodiments of the invention are shown. This invention, however, may be embodied in many different forms and should not be construed as limited to the embodiments set forth herein. Rather, these embodiments are provided so that this disclosure will be thorough and complete, and will fully convey the scope of the invention to those skilled in the art. In the drawings, like numbers refer to like elements throughout.

FIG. 1 is a schematic representation of an embodiment of the present invention disposed in a surgical application for example, an insufflation system utilizing a trocar device for laparoscopic surgical procedures. Typically, a gas supply or pump 1 provides pressurized gas (for example $CO_2$) via conduit 2 to an input port 6 of bypass valve 10. Bypass valve 10 is connected in parallel with surgical device 3 and regulates the flow of such gas from supply 1 to surgical device 3. Surgical device 3 directs outlet gas to an inlet or vacuum port of pump 1 via return line 5 which is likewise connected to outlet port 7 of valve 10. Thus, the system provides pressurized gas to a patient's abdomen using a closed system.

As noted above, laparoscopic surgical procedures utilize pressurized gas supplied to a patient's abdominal cavity. A sensing line 4 is connected between the surgical device 3 and bypass valve 10 to detect changes in this abdominal pressure. Bypass valve 10 is used to balance or regulate the flow of pressurized $CO_2$ gas to a patient's abdomen via surgical device 3 or a separate apparatus used to provide pressurized gas to a patient's abdomen. In particular, abdominal pressure values during surgical procedures vary, but may be within the range of 8-15 mmHG. Bypass valve 10 may be configured to allow a certain amount of pressurized gas from pump 1 to flow to the abdominal cavity via surgical device 3 to maintain the desired pressure value. By regulating the amount of gas bypassed from inlet port 6 to outlet port 7, a desired amount of pressurized $CO_2$ is supplied from pump 1 to surgical device 3. Bypass valve 10 maintains the supply of pressurized gas to the abdominal cavity and detects pressure changes of approximately ±1 mmHG. As the pressure in the abdominal cavity increases to unsafe levels outside an acceptable range, sensing line 4 provides an increase pressure supply to bypass valve 10. An increase in pressure may be caused by, for example, the introduction of laparoscopic instruments into a patient's abdomen. This initiates bypass valve 10 to open further which bypasses pressurized gas from pump 1 through valve 10 via input port 6 to output port 7. In this manner, pressurized gas from pump 1 is diverted away from surgical device 3 through bypass valve 10 back to pump 1, thereby reducing the supply of pressurized gas to a patient's abdomen. Conversely, as the pressure in the abdominal cavity decreases below an acceptable range, sensing line 4 provides a reduced pressure supply to bypass valve 10. This initiates bypass valve 10 to close further reducing the flow of gas from inlet port 6 to outlet port 7 and directing more pressurized gas to surgical device 3. In this manner, the supply of pressurized gas from pump 1 to surgical device 3 via bypass valve 10 is regulated to maintain a desired insufflation pressure.

Figure 2:
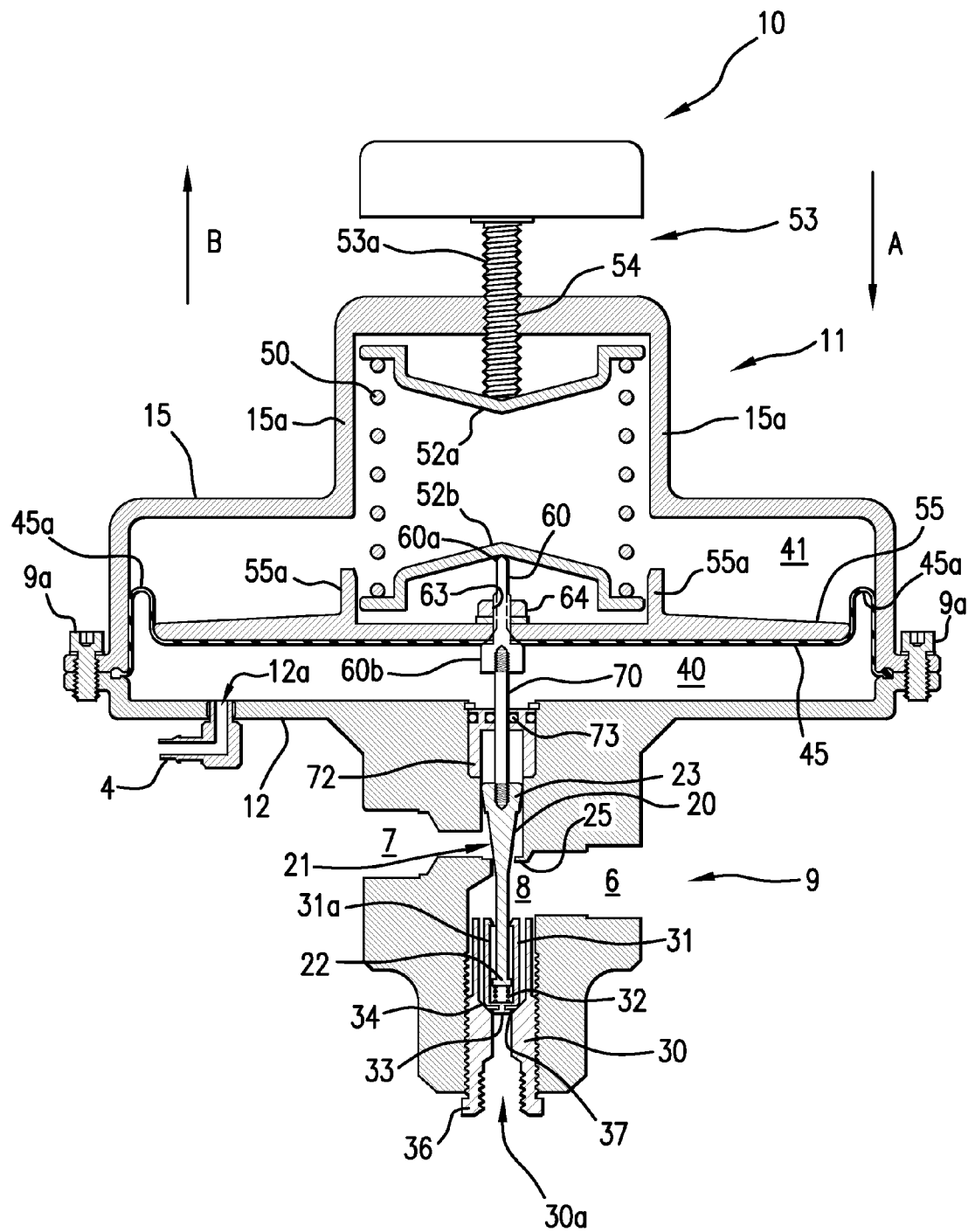
FIG. 2 is a cross sectional view of a diaphragm controlled bypass valve in an open or bypass position in accordance with the present invention.

FIG. 2 is a cross sectional view of an embodiment of the diaphragm controlled bypass valve 10 generally defined by a needle valve portion 9 and a diaphragm valve portion 11. Needle valve portion 9 includes housing 12 and diaphragm portion 11 includes housing 15 each of which have a substantially circular perimeter. Needle valve housing 12 is connected to diaphragm valve housing 15 via threaded fasteners 9a to provide air tight chambers within the valve housings.

Needle valve portion 9 includes an inlet port 6 and outlet port 7 which define valve pathway 8 through needle valve housing 12. Inlet port 6 and outlet port 7 define the opening and closing of bypass valve 10. Needle valve portion 9 further includes a valve closure mechanism in the form of needle valve pin 20 which is disposed vertically within valve pathway 8. Pin 20 is defined by angled central portion 21, proximal end 22 and distal end 23. Angled central portion 21 communicates circumferentially with valve seat area 25 of housing 12 to define an opening and closing of needle valve 9. For example, FIG. 2 illustrates bypass valve 10 in an open position such that angled portion 21 of pin 20 is displaced upward and off valve seat 25. As pin 20 moves off of seat 25, pressurized gas flows from input port 6 through pathway 8 to output port 7. In this manner, a portion of pressurized gas from pump 1 supplied to bypass valve 10 is bypassed away from surgical device 3 and returns to the inlet side of pump 1.

Bypass valve 10 also includes an automatic relief mechanism assembly 30 threadedly disposed within aperture 30a of needle valve housing 12. Automatic relief mechanism is configured to rapidly bypass pressurized gas supplied from pump 1 if the pressure in a patient's abdomen gets exceedingly high and a bypass port, in addition to outlet port 7, is required to redirect the supply of pressurized gas. Assembly 30 includes a threaded housing 36 which receives piston 31. Threaded housing 36 is engaged by lower threaded portion of valve housing 12 and the position of housing 36 within aperture 30a may be customized by tightening assembly 30 within valve housing 12. Piston 31 is defined by a vertical wall 31a and a transverse angled lower wall 33. Proximal end 22 of needle valve pin 20 is positioned within piston 31 and more particularly within the space formed by vertical wall 31a and transverse lower wall 33. A light weight spring coil 32 is disposed within piston 31 between proximal end 22 of needle valve pin 20 and transverse angled lower wall 33 to provide a bias force against pin 20. Transverse angled lower wall 33 contacts corresponding angled seat 34 of housing 36 to create a seal there between to close aperture 30a. A seal element 35 may be disposed on the angled lower wall to engage the angled seat 34 of the housing 36. The position of assembly 30 within aperture 30a may be modified by threading assembly 30 upward in direction B within needle housing 12 to accommodate a particular pressure setting or application. This in-turn varies the displacement of proximal end 22 of pin 20 within piston 31 and the corresponding biasing of spring coil 32. Needle valve housing 12 further includes a bore 12a through which sensing line 4 is connected. As stated earlier, sensing line 4 supplies pressure from surgical instrument 3 to chamber 40.

Diaphragm valve portion 11 is defined by housing or spring chamber 15 which includes diaphragm 45, spring coil 50 and pressure plate 55. Within housing 15, chamber 41 also includes spring plates 52a and 52b disposed at a top and bottom end, respectively of spring coil 50. Diaphragm 45 may be, for example, a convoluted diaphragm disposed between and extending around the circumference of housing 15 and is attached thereto between diaphragm housing 15 and needle housing 12 to create a seal between chambers 40 and 41. Diaphragm 45 is disposed between pressure plate 55 and Y coupler 60 and has a surface area, for example, of 20 in². Of course, alternative diaphragm sizes and configurations may be used to accommodate various pressure sensitivities. The diameter and surface area of diaphragm 45 is typically greater than the diameter of housing 15 such that diaphragm portion 45a is folded upward toward chamber 41. This portion 45a or a portion thereof is engaged when pressure in chamber 40 increases sufficiently to displace diaphragm 45 in direction B and maintains the pressure in chamber 40.

Pressure plate 55 has a diameter slightly less than the diameter of diaphragm 45 to allow for diaphragm portion 45a to be disposed between the edge of pressure plate 55 and housing 15. Pressure plate 55 includes an upwardly extending stop 55a positioned such that the top portion of stop 55a aligns with a vertical wall portion 15a of housing 15. This placement of stop 55a prevents excessive upward displacement of plate 55 greater than the surface area of diaphragm 45 (including portion 45a). In particular, as diaphragm 45 moves upward in direction B, pressure plate 55 is likewise displaced against spring 50 via spring plate 52b which eventually forces stop 55a to contact housing 15 at vertical wall 15a. Alternative stop mechanisms may be employed to prevent excessive movement of diaphragm 45 within chamber 41. As is evident from this description, the volume of chambers 40 and 41 change with movement of diaphragm 45 downward in direction A and upward in direction B. In particular, as the pressure increases in chamber 40 via sensing line 4, diaphragm 45 is forced upward in direction B, thereby increasing the volume of chamber 40 and decreasing the volume of chamber 41. Conversely, as the pressure decreases in chamber 40 via sensing line 4, diaphragm 45 moves downward in direction A, thereby decreasing the volume of chamber 40 and increasing the volume of chamber 41. Although the volume of chamber 41 may change, the pressure therein remains at atmosphere. In particular, a bore (not shown) is present in a wall (for example wall 15a) of housing 15 for venting the pressure in chamber 41 to atmosphere as diaphragm 45 moves in direction B. This allows the pressure in chamber 41 to remain at atmosphere and the source of the downward force applied to diaphragm 45 in direction A to be provided by spring 50.

Spring coil 50 is disposed between spring plates 52a, 52b. Adjustment screw 53 has a lower extending threaded portion 53a disposed through housing aperture 54 which contacts upper spring plate 52a. The lower extending portion 53a of adjustment screw 53 forces spring plate 52a downward in direction A providing a biasing force against coil spring 50 and spring plate 52b. The bias of spring coil 50 and the placement of pressure plate 55 may be adjusted via adjustment screw 53 based on the desired pressure regulation parameters provided by diaphragm 45 within chamber 41. In particular, by tightening adjustment screw 53, threaded portion 53a forces spring plate 52a against coil spring 50. The bias of spring 50 applies a force against spring plate 52b which forces pressure plate 55 in direction A against diaphragm 45. This displacement of diaphragm 45 downward in direction A is limited to the point where needle valve piston 20 engages seat 25. Similarly, by loosing adjustment screw 53, threaded portion 53a reduces the force against spring plate 52a and coil spring 50. This allows spring plate 52b, pressure plate 55 and diaphragm 45 to move upward in direction B. This displacement of diaphragm 45 upward increases the volume of chamber 40. By adjusting screw 53 and the force from spring 50 onto pressure plate 55, the response time associated with a pressure change received into chamber 40 and the corresponding displacement of diaphragm 45 may be modified.

The Y-shaped coupler 60 has a first end 60a and a second end 60b. First end 60a contacts spring plate 52b and receives the downward biasing force from coil spring 50. Coupler 60 extends through a bore centrally located in diaphragm 45 as well as a similarly aligned bore through pressure plate 55. Coupler 60 may have a threaded portion 63 which is used to hold coupler 60 in position through pressure plate 55 and diaphragm 45 using fastening nut 64. Second end 60b has a Y-shape end which receives a first end of pull shaft 70. U-shaped collar 72 is positioned around passageway 8 and includes a centrally located bore through which shaft 70 extends. The bore of u-shaped collar 72 may include o-rings 73 used to isolate the pump outlet pressure entering port 6 from the pressure in chamber 40. A second end of shaft 70 is connected to distal end 23 of pin 20 such that as diaphragm 45 is displaced in directions A or B, pin 20 is likewise displaced through the movement of shaft 70 connected to Y-shaped coupler 60. Obviously, various configurations may be employed to provide a coupling mechanism between diaphragm 45 and pin 20. Although not illustrated in FIG. 2, the width of distal end 23 of pin 20 is slightly less then the width of valve pathway 8. This allows gas received via inlet port 6 to feed into pathway 8, around distal end 23 of pin 20 to U-shaped collar 72.

In operation, needle valve 9 bypasses pressurized gas from pump 1 away from surgical instrument 3 maintaining the system in a balanced state whereby sufficient pressure is supplied to or bypassed away from a patient's abdomen. In a balanced state, needle valve 9 and more particularly, pin 20 remains open or displaced from seat 25 allowing a portion of pressurized gas to bypass from inlet port 6 to outlet port 7 while also allowing a portion of the pressurized gas to be supplied to surgical instrument 3. Pressure from sensing line 4 is supplied to chamber 40. Diaphragm 45 senses this change in pressure. The pressure against diaphragm 45 is controlled by adjustment screw 53 in combination with the bias force from spring 50 and pressure plate 55. The change in pressure in chamber 40 either displaces diaphragm 45 in direction A or B. For example, if sensing line 4 provides an increase in pressure to chamber 40, diaphragm 45 moves in direction B biased against spring 50 and spring plates 52a, 52b. This increase in pressure indicates that a higher pressure level is in a patient's abdomen and that gas supplied by pump 1 needs to be diverted away or bypassed from surgical instrument 3. Displacement of diaphragm 45 in direction B lifts pin 20 further away from seat 25 thereby allowing more pressurized gas to flow from inlet port 6 through pathway 8 to outlet port 7. If sensing line 4 provides a decrease in pressure to chamber 40, diaphragm 45 moves in direction A biased away from spring 50 and spring plates 52a, 52b. This decrease in pressure indicates that a lower pressure level is present in a patient's abdomen and that additional pressurized gas needs to be supplied to surgical instrument 1. Displacement of diaphragm 45 in direction A pushes down on coupler 60 which moves shaft 70 against pin 20. As pin 20 moves in direction A, angled central portion 21 engages seat 25 thereby restricting pathway 8 and preventing the flow of gas from inlet port 6 to outlet port 7. By restricting the bypass of pressurized gas through valve 10, more pressurized gas is supplied to a patient's abdomen via surgical instrument 3. In this manner, bypass valve 10 combines the pressure regulation feature of a diaphragm valve with the precise operation and control of a needle valve to regulate the flow of pressurized gas for surgical procedures.

Figure 3:
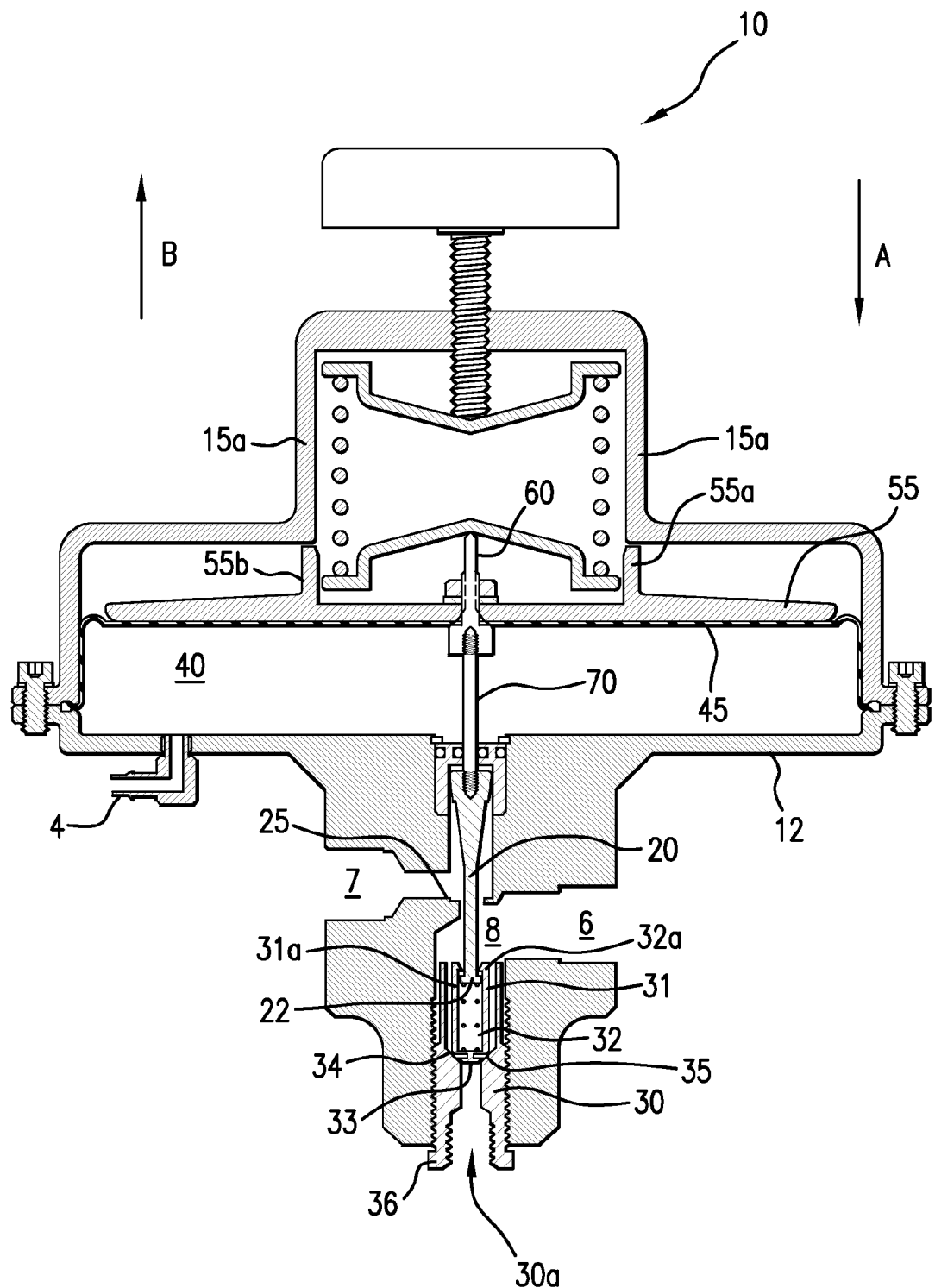
FIG. 3 illustrates an exploded view of the bypass valve shown in FIG. 2 where an automatic relief mechanism assembly is in an open position.

FIG. 3 is a schematic view of bypass valve 10 illustrating automatic relief mechanism assembly 30 in an open position. Again, movement of diaphragm 45 in this manner indicates a significant increase in pressure supplied to a patient's abdomen requiring a rapid bypass of pressurized gas through bypass valve 10. As pressure in chamber 40 increases significantly, diaphragm 45 may be displaced in direction B a distance sufficient to engage diaphragm appendage portion 45a. As diaphragm 45 moves upward in direction B, stop 55a contacts vertical wall portion 15a. This movement of diaphragm 45 pulls shaft 70 and coupler 60 likewise upward, thereby pulling the proximal end 22 of pin 20 upward within piston 31. Vertical wall 31a of piston 30 includes clip portion 32a which extends inwardly and engages proximal end 22 of pin 20 which may have a T-shape configuration. This engagement of proximal end 22 and clip portion 32a pulls piston 30 upward in direction B which breaks the seal formed between transverse angled wall 33 of piston 31 and angled wall 34 of housing 36. This opens aperture 30a and allows additional pressurized gas to flow there through to atmosphere. In addition, since pin 20 is likewise pulled away from seat 25, pressurized gas is also bypassed through pathway 8 in addition to the gas flowing through automatic relief mechanism assembly 30. In this manner, an increase in pressurized gas in a patient's abdomen requiring rapid bypass is accommodated through the opening of the needle valve as well as the opening of aperture 30a of automatic relief mechanism assembly 30.

While the present invention has been disclosed with reference to certain embodiments, numerous modifications, alterations and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:
1. A diaphragm controlled bypass valve comprising:
   a first valve housing having an inlet, an outlet and a flow pathway defined between said inlet and said outlet;
   a needle valve having a needle valve pin disposed at least partially within said flow pathway, said needle valve pin having proximal and distal ends and an angled central portion;

a valve seat disposed within said first valve housing configured to receive the angled central portion of said needle valve pin to close said flow path;

a second valve housing connected to said first valve housing;

a diaphragm extending radially within said second valve housing, said diaphragm and said second valve housing defining a first pressure chamber there between;

a second pressure chamber defined between said diaphragm and said first valve housing;

a sensing line connected to a bore in said second pressure chamber, said sensing line configured to provide a pressure change to said second pressure chamber to displace said diaphragm within said first pressure chamber; and a shaft assembly coupled to said diaphragm and said needle valve pin such that displacement of said diaphragm moves said shaft assembly to open and close said needle valve;

wherein said outlet is a first outlet and said first valve housing further comprising a second outlet; the diaphragm controlled bypass valve further comprising an automatic relief mechanism disposed within said second outlet.

2. The diaphragm controlled bypass valve of claim 1 further comprising a bias spring disposed within said valve second housing, said spring exerting a force against said diaphragm.

3. The diaphragm controlled bypass valve of claim 1 said automatic relief mechanism comprising:

a relief housing threadedly engaged within said second outlet;

a piston disposed within said relief housing, said piston having a cavity defined by a vertical wall and a transverse lower wall, said needle pin having a proximal end disposed within said piston cavity;

a valve seat configured within said relief housing, said transverse wall of said piston engaging said valve seat such that upward movement of said piston off said valve seat permits flow of gas from said inlet through said second outlet.

4. The diaphragm controlled bypass valve of claim 3 further comprising an o-ring disposed between said transverse wall of said piston and said relief housing valve seat, said o-ring configured to provide a seal between said piston and said relief housing valve seat to prevent the flow of pressurized gas from said inlet through said second outlet.

5. The diaphragm controlled bypass valve of claim 3 further comprising a spring disposed between said proximal end of said needle pin and said transverse wall, said spring configured to provide a bias force against said proximal end of said needle pin.

6. The diaphragm controlled bypass valve of claim 3 wherein said vertical wall of said piston further comprising a retaining clip positioned at one end of said vertical wall, said retaining clip configured to engage said proximal end of said needle pin when said needle pin is pulled upward toward said diaphragm.

7. The diaphragm controlled bypass valve of claim 1 further comprising a pressure plate disposed within said second housing and in contact with said diaphragm.

8. The diaphragm controlled bypass valve of claim 7 wherein said shaft assembly comprising:

a coupler fixedly positioned through a centrally disposed bore in said diaphragm and said pressure plate; and a shaft having a first end connected to said coupler and a second end coupled to a distal end of said needle valve pin.

9. The diaphragm controlled bypass valve of claim 8 further comprising:

a first and second spring plates positioned with said second valve housing; and a coil spring disposed between said first and second spring plates, said coil spring and said first spring plate supplying a bias force against said coupler, said pressure plate and said diaphragm.

10. The diaphragm controlled bypass valve of claim 9 wherein said pressure plate having a first diameter and said diaphragm having a second diameter, said first diameter less than said second diameter.

11. The diaphragm controlled bypass valve of claim 10 further comprising an adjustment mechanism positioned through a bore in said second valve housing and in contact with said second spring plate, said adjustment mechanism configured to apply a force against said diaphragm via said first spring plate, said spring coil, said coupler and said pressure plate.

12. The diaphragm controlled bypass valve of claim 7 wherein said second valve housing has at least one vertical wall, said pressure plate further comprising at least one vertically extending stop portion aligned with said at least one vertical wall, said stop portion engaging said vertical wall when said diaphragm is displaced a predetermined distance within said second pressure chamber.

13. A bypass valve comprising:

a first valve housing having an inlet, an outlet and a flow pathway defined between said inlet and said outlet;

a valve closure mechanism disposed at least partially within said flow pathway, said closure mechanism configured to be in a first position to allow process media to flow from said inlet to said outlet via said flow pathway and in a second position to prevent process media to flow from said inlet to said outlet, said valve closure mechanism comprising a needle valve pin and a valve seat, said needle valve pin having proximal and distal ends and an angled central portion, said valve seat configured to receive the angled central portion of said needle valve pin to close said flow path in said second position;

a second valve housing connected to said first valve housing;

a diaphragm extending radially within said second valve housing, said diaphragm and said second valve housing defining a first pressure chamber there between, said diaphragm coupled to said needle valve pin by a shaft assembly;

a second pressure chamber defined between said diaphragm and said first valve housing; and a sensing line connected to said second pressure chamber, said sensing line configured to provide a pressure change to said second pressure chamber to displace said diaphragm within said first pressure chamber wherein displacement of said diaphragm controls said valve closure mechanism to move from said first position to said second position;

wherein said outlet is a first outlet and said first valve housing further comprising a second outlet, said bypass valve further comprising an automatic relief mechanism disposed within said second outlet.

14. The bypass valve of claim 13 wherein said distal end said of said needle valve pin received within an opening in said first valve housing, said distal end having a width smaller than a width of said opening to allow process media communication past said proximal end.

15. Bypass valve of claim 13 said shaft assembly disposed between said diaphragm and said needle pin such that displacement of said diaphragm within said second pressure chamber moves said shaft assembly from said first position to said second position.

16. The bypass valve of claim further 13 comprising a bias spring disposed within said second valve housing, said spring exerting a force against said diaphragm.

17. The bypass valve of claim 13 further comprising a pressure plate disposed within said second valve housing and in contact with said diaphragm.

18. The bypass valve of claim 14 wherein said automatic relief mechanism further comprising:

- a relief housing threadedly engaged within said second outlet;
- a piston disposed within said relief housing, said piston having a cavity defined by a vertical wall and a transverse lower wall, said needle pin having a proximal end disposed within said piston cavity;
- a valve seat configured within said relief housing, said transverse wall of said piston engaging said valve seat such that upward movement of said piston off said valve seat permits process flow from said inlet through said second outlet.

* * * * *